Nov. 11, 1952 T. B. STRIBLING, JR Plant Pat. 1,144

PEACH TREE

Filed Oct. 17, 1950

WITNESS

Addison T. Avery

INVENTOR

Thomas B. Stribling Jr

Webster & Webster

ATTYS.

Patented Nov. 11, 1952

Plant Pat. 1,144

UNITED STATES PATENT OFFICE 1,144

PEACH TREE

Thomas Burton Stribling, Jr., Merced, Calif.

Application October 17, 1950, Serial No. 190,505

1 Claim. (Cl. 47—62)

The present discovery relates to a new and distinct variety of peach tree which bears early yellow-fleshed freestone fruit, which fruit is of excellent character for market or dessert use.

The new and distinct variety of peach tree herein described was originated and successfully asexually propagated in the following manner:

A substantial number of the seeds of the July Elberta variety were planted in January of 1945 in applicant's growing plot near Le Grand, Merced County, California.

In June of 1945 the resulting seedlings, then very small, were cut and budded onto year-old root stock trees; such top-worked root stock trees having borne several fruit in the harvest season of 1946. Such initial fruit, along with that borne by the trees in the harvest season of 1947, was given close and careful observation in both years, and the present variety—because it evidenced very substantial promise by reason of certain new and distinctive pomological characteristics thereof, as will hereinafter appear—was selected for the purpose of further observation, and propagation.

In 1947 this variety of peach tree was top-worked, at said growing plot, onto a young experimental orchard, which fruited first in 1949; such fruit, and the fruit of the subsequent harvest seasons of 1950 and 1951 from said orchard, having been the subject of careful comparisons with the fruit of the parent tree. As a result of such comparisons it has been definitely ascertained that the asexual reproductions of the variety carry forward each and every one of the novel features of said parent tree and its fruit.

The instant variety of peach tree carries forward the vigorous growing habit and consistent bearing qualities of the parent July Elberta peach (early Elberta or July Elberta), and also has its freestone fruit; the fruit being only slightly more adherent to the pit than the July Elberta. The present variety has a similar, if not improved, flavor relative to that of the parent July Elberta, but is distinguished in that it has a rounder, more spherical shape, less down, and a slight tendency to be softer. Most important, the present variety bears fruit which ripens thirty days earlier than the parent July Elberta, which is the major commercial advantage.

In outer appearance the highly colored skin of the present variety is similar to that of the Red Haven, which is today's leading early market yellow fleshed freestone peach. It differs from the Red Haven in that it has a rounder, more spherical shape, and ripens approximately two weeks earlier. This ability to reach the market two weeks earlier, with comparative coloring, size, flavor, and over-all quality relative to the Red Haven peach is considered a very valuable feature.

The herein claimed variety of peach tree bears fruit which ripens two or three days later than the Florence, the earliest bearing peach tree grown commercially at the present time, but has the distinguishing commercial advantages over the Florence peach (which has white flesh) in that it has clear yellow flesh, larger size, less down, more colorful skin, and greater disease resistance.

Since its discovery, the new variety has been successfully asexually reproduced, with the reproductions carrying forward all of the distinctive characteristics of the parent tree and its fruit.

Figures 1, 2:
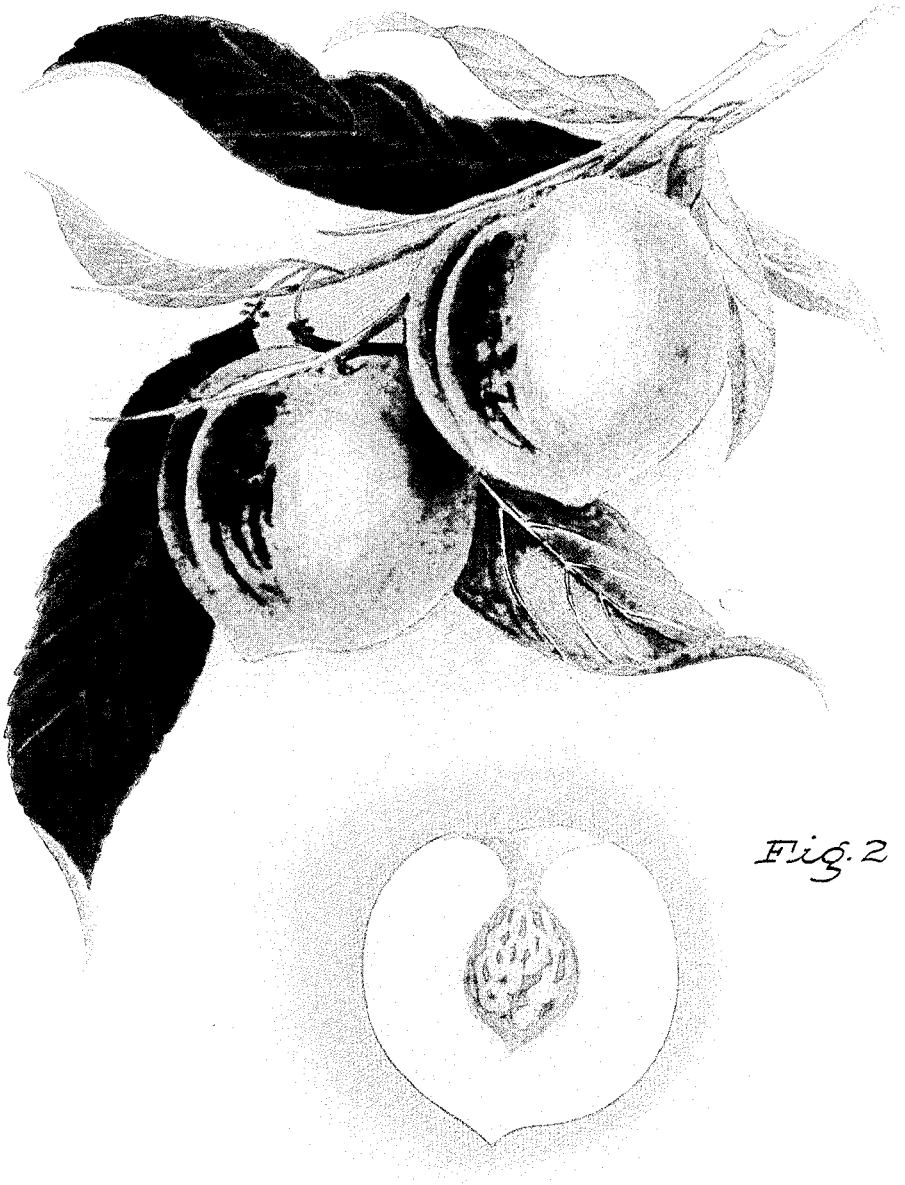
Fig. 1 is a perspective view of a pair of the peaches of the present variety in connection with twigs and leaves.
Fig. 2 is a sectional view taken axially of one of the peaches, with the stone exposed.

Referring now in detail to the new and distinct variety of peach tree and its fruit, the following is a specific description, in outline, of the same; detailed identification of colors being by reference to Maerz and Paul Dictionary of Color:

Tree: Large; vigorous; upright; dense; round topped; hardy; very productive; regular bearer.

Trunk: Medium size; medium texture.

Branches: Medium size; medium texture. Color—brown.

*Lenticels.*—Medium number; medium size.

Leaves: Average length, 7''; average width, 1½''. Medium size; acuminate; lanceolate; acutely pointed; medium thick; smooth. Color—dark green (24–L–7) on top with lighter green (22–C–7) on under side. Leaf twigs—color: light green (20–J–6).

*Margin.*—Crenate finely serrate.

*Petiole.*—Medium length; medium thickness.

*Glands.*—Average number—five. Alternate; medium size; reniform. Color—green. Position—on petiole and blade. Stipules lacking.

Flower buds: Half hardy; medium size; medium length; conic. The flowers are self-fertile; the stamens having red anthers.

Flowers: Dates of first and full bloom—March 1st and March 6th, respectively. Medium blooming period compared with other varieties. Small size. Color—pink.

Fruit: Dates of first and last picking—June 8th and 18th, respectively. Maturity when described—eating, June 11, 1950.

*Size.*—Medium—variable. Averages 2⅛″ axially and 2½″ transversely in the suture plane.

*Form.*—Uniform; symmetrical; globose.

*Suture.*—An inconspicuous line; shallow, extending from base but discontinuous at apex, with slight depression beyond pistil point.

*Ventral surface.*—Rounded slightly; lipped toward base on both sides. Lips—equal.

*Cavity.*—Flaring; elongated in suture plane, with suture showing on both sides. Average depth, ½″; average breadth, 1⅛″.

*Base.*—Rounded.

*Apex.*—Short to prolonged.

*Pistil point.*—Apical.

Skin: Medium thick; tender, free; slight tendency to crack.

*Color.*—Reddish mottling and streaks (5–L–6 to 6–L–6) over yellow (10–K–6).

*Down.*—Scant; does not roll up when rubbed.

Flesh:

*Color.*—Yellow (9–4–K).

*Surface of pit cavity.*—Pale pink with pink fibers. Clear yellow to pit—pinkish around pit.

*Amygdalin.*—Moderate.

*Juice.*—Abundant; rich.

*Texture.*—Firm to medium; crisp; melting.

*Fibers.*—Fine; tender.

*Ripens.*—Evenly.

*Flavor.*—Sub-acid; mild; delicate.

*Aroma.*—Average.

*Eating quality.*—Good to best.

Stone: Free.

*Fibers.*—Short; parts from flesh smoothly when fully ripe; retains short fiber-like threads along ridges. Small size—average 1¼″ in length, ⅞″ in breadth; and ¾″ in thickness.

*Form.*—Obovoid; cunate toward base.

*Base.*—Straight.

*Hilum.*—Narrow; oblong.

*Apex.*—Acute.

*Sides.*—Equal.

*Surface.*—Regularly furrowed throughout; ridged toward apex; pitted toward base.

*Ridges.*—Jagged toward apex.

*Pits.*—Angular.

*Ventral edge.*—Thick with wing throughout.

*Dorsal edge.*—Full, with shallow narrow groove throughout.

*Ridges.*—Continuous.

*Color.*—Light brown (12–E–7).

*Tendency to split.*—Slight.

Use: Early market; local; dessert.

Keeping quality: Good to medium.

Shipping quality: Good to medium.

The fruit of the new variety is excellent for market and dessert use, by virtue of its highly colored freestone fruit (reddish mottling and streaks over a yellow ground), and its flavorsome yellow flesh; yellow flesh being a distinct commercial advantage in the early ripening freestone peach.

In relation to the July Elberta and Red Haven, the present variety ripens thirty days and two weeks earlier, respectively; the ripening period being only two or three days later than the Florence. Also, in comparison to the July Elberta, Red Haven, and Florence, the fruit of the present variety is rounder, with less down; being slightly softer than the July Elberta, and somewhat larger in size than the Florence.

The tree and its fruit herein described may vary in slight detail due to climatic and soil conditions under which the variety may be grown.

To applicant's knowledge Red Haven and Florence varieties of peach trees are unpatented; July Elberta being the subject of United States Plant Patent No. 15.

Having thus described my invention, I claim:

A new and distinct variety of peach tree, substantially as described and illustrated, bearing yellow fleshed, freestone fruit, having a skin which is yellow in ground color, mottled and streaked to a substantial extent in red, characterized by a ripening period approximately thirty days earlier than the July Elberta; approximately two weeks earlier than the Red Haven; and approximately two or three days later than the Florence; being further distinguished from the July Elberta by rounder form and less down; from the Red Haven by rounder form; and from the Florence by larger size, rounder form, less down, yellow instead of white flesh.

THOMAS BURTON STRIBLING, JR.

No references cited.